United States Patent [19]
Strosberg et al.

[11] Patent Number: 6,071,747
[45] Date of Patent: Jun. 6, 2000

[54] IMMORTALIZED CELL LINES FROM HUMAN ADIPOSE TISSUE, PROCESS FOR PREPARING SAME AND APPLICATIONS THEREOF

[75] Inventors: Arthur Donny Strosberg, Paris; Vladimir Zilberfarb, Villebon-sur-Yvette, both of France

[73] Assignee: Centre National de la Recherche Scientifique-CNRS, Paris, France

[21] Appl. No.: 08/945,654

[22] PCT Filed: Apr. 25, 1996

[86] PCT No.: PCT/FR96/00634

§ 371 Date: Jan. 5, 1998

§ 102(e) Date: Jan. 5, 1998

[87] PCT Pub. No.: WO96/34100

PCT Pub. Date: Oct. 31, 1996

[30] Foreign Application Priority Data

Apr. 25, 1995 [FR] France .................................. 95 04922

[51] Int. Cl.⁷ .............................. C12N 15/87; C12N 5/08
[52] U.S. Cl. .......................... 435/467; 435/366; 435/377; 435/455
[58] Field of Search ..................... 435/366, 467, 435/377

[56] References Cited

FOREIGN PATENT DOCUMENTS 409696  1/1991  European Pat. Off. .

OTHER PUBLICATIONS

Benito et al., Experimental Cell Research 209:248–254 (1993).

Shigeru Yasumoto, "Hormonal Regulation of the Transformation Phenotype in Simian Virus 40–Transformed Rat Embryonic Preadipose Cell Lines", *Molecular and Cellular Biology*, vol. 4, no. 4, Apr. 1984, pp. 712–721.

Kazuyuki Tobe et al., "Differential effects of DNA tumor virus nuclear oncogene products on adipocyte differentiation", *FEBS Letters*, vol. 215, No. 2, May 1987, pp. 345–349.

Jun Ninomiya–Tsuji et al., "Tumor necrosis factor–induced c–myc expression in the absence of mitogenesis is associated with inhibition of adipocyte differentiation", *Proc. Natl. Acad. Sci. USA*, vol. 90, Oct. 1993, pp. 9611–9615.

Bruno Feve et al., "Differential Regulation of $\beta_1$– and $\beta_2$–Adrenergic Receptor Protein and mRNA Levels by Glucocorticoids during 3T3–F442a Adipose Differentiation", *The Journal of Biological Chemisty*, vol. 265, No. 27, Sep. 25, 1990, pp. 16343–16349.

Bruno Feve et al., "Atypical β–Adrenergic Receptor in 3T3–F442A Adipocytes—Pharmacological and Molecular Relationship with the Human $\beta_3$–Adrenergic Receptor", *The Journal of Biological Chemistry*, vol. 266, No. 30, Oct. 25, 1991, pp. 20329–20336.

Stephane Krief et al., "Transcriptional Modulation by n–Butyric Acid of $\beta 1$, $\beta 2–$, and $\beta 3$–Adrenergic Receptor Balance in 3T3–F442A Adipocytes", *The Journal of Biological Chemistry*, vol. 269, No. 9, Mar. 4, 1994, pp. 6664–6670.

Kozak et al., "Norepinephrine–dependent selection of brown adipocyte cell lines", Database Medline File Server STN Karlsruhe, No. 94130843, and *Endocrinology*, 134 (2) 906–13, Feb. 1994.

*Primary Examiner*—Remy Yucel
*Attorney, Agent, or Firm*—Alston & Bird LLP

[57] ABSTRACT

Immortalized cell lines from human adipose tissue, process for preparing same and applications thereof as a study model for the physiopathology of the metabolism and particularly for obesity and diabetes, as tools for developing drugs for the treatment of disease states linked to metabolic disorders such as obesity and diabetes, and as drugs. The cell lines are formed of pre-adipocytes containing a nucleic acid fragment including at least one fragment immortalizing a viral oncogene, and at least one promoter selected from the group containing a promoter of said viral oncogene and a human vimentine gene regulatory region fragment. They express at least one of the following proteins: the $\beta 1$ and $\beta 2$-adrenergic receptors, the uncoupling protein (UCP), the glucose transporters, Glut1 and Glut 4 and lipoprotein lipase (LPL). They are capable of being converted into mature adipocytes which product fat and further express the $\alpha 2_A$ and $\beta 3$-adrenergic receptors as well as the expression product of the Ob gene, and have an inverted Glut4/Glut1 ratio in relation to said immortalized pre-adipocytes.

12 Claims, 4 Drawing Sheets

IMMORTALIZED CELL LINES FROM HUMAN ADIPOSE TISSUE, PROCESS FOR PREPARING SAME AND APPLICATIONS THEREOF

This application is a national stage application of PCT International Application No. PCT/FR96/00634 filed on Apr. 25, 1996, and claims priority to French Application No. 95/04922 filed on Apr. 25, 1995, which is incorporated herein by reference in its entirety.

The present invention relates to immortalized cell lines from human adipose tissue, to the process for their preparation and to their applications as a model for studying the physiopathology of the metabolism, especially obesity and diabetes, as tools for the development of drugs for the treatment of pathological conditions associated with metabolic disorders such as obesity and diabetes, and as drugs.

Obesity and diabetes constitute major health problems in the West and important risk factors in early mortality. The factors considered to be responsible for the development of obesity and diabetes are not yet all well known. However, it is now widely acknowledged that thermogenesis defects (for example defects of energy dissipation in the form of heat, with the consequence of lipid accumulation) are involved in the mechanisms of obesity; it is also widely acknowledged that adipose tissue, especially brown adipose tissue, is the principal effector of optional chemical thermogenesis.

Adipose tissue (brown and white) essentially consists of adipocytes (¾ of the total number of adipose tissue cells). The other cells present in adipose tissue belong especially to precursor cells, also called interstitial cells (lipid-free cells), and comprise particularly adipoblasts (lipid-free mesenchymal cells) and preadipocytes (lipid-free esterase-positive cells).

White adipose tissue (or WAT) is considered to be a different organ from brown adipose tissue (or BAT); these two adipose tissues are distinguished especially by the fact that their precursor cells are different; the presence of uncoupling proteins (or UCP) is specific to BAT (brown adipose tissue). As regards brown adipose tissue more particularly, the chronology of the cellular differentiation appears to be as follows: interstitial cells, brown adipocytes with a low level of differentiation, and mature brown adipocytes. Brown adipocytes are characterized by the presence of droplets of triglycerides and numerous mitochondria and by the presence of a particular protein, namely the above-mentioned uncoupling protein.

Stimulation of the proliferation and differentiation of brown adipose tissue depends especially on the β-adrenergic receptors. The human β3-adrenergic receptor has been characterized in the white adipose deposits of adults and in the brown adipose tissue of newborns and patients suffering from pheochromocytoma.

BAT is a tissue specializing in energy dissipation in the form of heat. It is found in most newborn mammals.

It is the major site of energy storage and mobilization; its role as an endocrine, autocrine and intracrine organ has also been established.

Cell lines produced in mice [murine line 3T3, line F44-2A (Green et al., Cell, 1975, 5, 19–27 and Cell, 1976, 7, 105–113)], as well as stromal vascular cells of adipose tissue, have also been the object of study insofar as preadipocytes are present in the vascular-stromal compartment (G. Ailhaud et al., Int. J. Obesity, 1992, 16, (suppl. 2), S17–S21).

However, these different lines or cells are not suitable for studying the physiopathology of the human metabolism. Consequently, there is a need to control metabolic diseases, especially obesity and diabetes, in man, both from the pharmacological point of view (model for the pharmacological study of lipolytic agents) and from the therapeutic point of view.

Now, it has hitherto been impossible to obtain lines of human preadipocytes which are capable of being maintained in culture for a sufficiently long time to be able to serve effectively as a model for studying lipolytic agents, on the one hand, and also to be suitable for use as therapeutic agents (in gene therapy, for example), on the other hand. In fact, the experiments performed on human adipocytes in primary culture are difficult to reproduce and difficult to carry out systematically.

The Applicant consequently set itself the task of providing cell lines, from brown or white adipose tissue, which are useful both as a model for studying lipolytic agents and as therapeutic agents (hyper-expression of the uncoupling protein, for example) and which do not have the disadvantages of adipocytes in primary culture.

The present invention relates to cell lines from adipose tissue, characterized in that:

they consist of preadipocytes containing a nucleic acid fragment comprising at least one immortalizing fragment of a viral oncogene and at least one promoter selected from the group comprising the promoter of said viral oncogene and a fragment of the regulatory regions of the human vimentin gene, they express at least one of the following proteins: β1- and β2-adrenergic receptors, uncoupling protein (UCP), glucose transporters Glut1 and Glut4, and lipoprotein lipase (LPL), and they are capable of being converted to mature adipocytes which produce lipids (fat), additionally express the ($\alpha2_A$- and β3-adrenergic receptors as well as the expression product of the Ob gene, and have an inverted ratio Glut4/Glut1 relative to said immortalized preadipocytes.

The specific markers of mature adipocytes (brown adipose tissue and white adipose tissue) are especially Glut4, adipsin, LPL, lipolytic enzyme (hormone sensitive lipase: HSL), β1-, β2- and β3-adrenergic receptors and the expression product of the Ob gene.

In one advantageous embodiment, said lines are derived from brown adipose tissue.

In this advantageous embodiment of said lines, the immortalizing fragment consists of a fragment of the SV40 T oncogene coding for the T antigen of the SV40 virus.

Also in this embodiment of said lines, the promoter is selected from the SV40 T oncogene promoter and the vimentin promoter, more particularly the nucleic acid fragment of the vimentin promoter between bases −878 and +93 of the regulatory sequence of vimentin.

In one advantageous provision of this embodiment, the nucleic acid fragment of the vimentin promoter comprises bases −830 to −539 and/or the fragment −540 to −140, located upstream of the CAP site.

Such lines, called PAZ-6, were deposited on 7th February 1995 under no. I-1531 in the Collection Nationale de Culture de Microorganismes (CNCM) held by the INSTITUT PASTEUR 28, rue du Dr Roux, 75724 Paris Cedex 15, France.

Such lines of immortalized human preadipocytes have at least the following properties:

they express at least the following proteins: β1- and β2-adrenergic receptors, uncoupling protein, Glut1 and Glut4, and lipoprotein lipase; and they are capable of being converted to mature adipocytes which:

produce multilobar fat, contain numerous mitochondria, express the $\alpha 2_A$- and $\beta 3$-adrenergic receptors and the expression product of the Ob gene, and have an inverted ratio Glut4/Glut1 relative to said immortalized preadipocytes.

A hybrid nucleic acid fragment (SV40 T oncogene associated with the vimentin promoter) has been described (European patent application 90402009.6). The introduction of this recombinant linear fragment into the nucleus of cells in primary cultures, such as muscle cells, epithelial cells and endothelial cells, is followed by an integration and by the expression of the large T antigen, inducing a cell proliferation and leading to permanent cell lines.

However, the studies of the prior art do not suggest the possibility that preadipocytes from human (brown or white) adipose tissue could in fact be immortalized, thereby retaining all their characteristics (markers and possibility of differentiation). It has actually never been possible to obtain any human line of this type, whether it be of pathological (for example cancerous) origin or experimental origin. On the contrary, numerous attempts at immortalization (H. HAUNER et al., J. Clin. Invest., 1989, 84, 1663–1670) have all failed, which is what has hitherto distinguished human adipocytes from numerous other cell types.

Now, unexpectedly, the immortalized preadipocyte lines according to the invention actually have the functional characteristics of human preadipocytes: expression of the preadipocyte markers and maturation into adipocytes under appropriate conditions, especially in the presence of insulin, glucocorticoids and optionally IGF-I.

In particular, the immortalized preadipocytes according to the invention make it possible to:

study the different steps of maturation of the differentiation into adipocytes: appearance of the specific adipocyte markers such as the $\alpha 2_A$- and $\beta 3$-adrenergic receptors, and presence of lipid droplets, analyze the influence of different culture conditions on the differentiation of adipocytes: insulin, glucocorticoids, triiodothyronine optionally associated with pioglitazone and its derivatives, $\beta$-adrenergic agonists, NPY, melatonin, etc., analyze the role of the expression product of the Ob gene in the differentiated and mature adipocytes according to the invention in thermogenesis, and study the receptors involved in the processes of lipolysis, such as the $\beta 2$- and $\beta 3$-adrenergic receptors, more realistically than CHO/$\beta 3$-AR cells allow.

The present invention further relates to a process for the preparation of immortalized preadipocytes from human (brown or white) adipose tissues, characterized in that it comprises converting preadipocytes from human (brown or white) adipose tissue by means of a nucleic acid sequence as defined above.

The present invention further relates to a process for the conversion of the preadipocytes according to the invention to mature adipocytes, which process is characterized in that it comprises the cultivation of the immortalized preadipocytes according to the invention in a medium containing at least insulin.

In one advantageous mode of carrying out said process, said medium also comprises at least one of the following compounds: glucocorticoid, triiodothyronine (T3) optionally associated with pioglitazone or its derivatives, $\beta$-adrenergic receptor agonists, NPY and melatonin.

Advantageously, the immortalized preadipocytes according to the invention also constitute a tool for selecting substances involved in the activation of lipolysis and/or thermogenesis; according to the invention, the process for the selection and identification of substances capable of regulating lipolysis and/or thermogenesis comprises:

bringing the immortalized preadipocytes according to the invention into contact with at least one substance capable of converting them to adipocytes, bringing the mature adipocytes obtained into contact with a substance which acts on at least one receptor of said mature adipocytes, such as the $\alpha 2_A$- or $\beta 3$-adrenergic receptors, the insulin and IGF receptors, the ACTH receptors and the glucose metabolism receptors (Glut1, Glut4), in order to modify lipolysis and/or thermogenesis, and detecting the formation of a complex of the ligand-receptor type.

Such a process therefore makes it possible to select ligands specific for the different receptors mentioned, namely the $\alpha 2_A$- or $\beta 3$-adrenergic receptors, the insulin and IGF receptors, the ACTH receptors and the glucose metabolism receptors (Glut1, Glut4) of the mature adipocytes, which ligands also act on the modification of lipolysis and/or thermogenesis.

The present invention further relates to a model for studying the proteins expressed by adipocytes, especially the $\alpha 2_A$- or $\beta 3$-adrenergic receptors, the insulin, IGF and ACTH receptors and the human glucose metabolism receptors (Glut1, Glut4), characterized in that it consists of mature adipocytes obtained from the immortalized preadipocytes according to the invention.

Such a model makes it possible to study, from a pharmacological point of view, the receptors involved in lipolysis and thermogenesis processes, which, when they exhibit anomalies, induce pathological conditions such as diabetes and/or obesity. Such a model, which is particularly close to the human physiological condition, makes it possible to identify ligands with a higher affinity for these receptors, and thus to develop drugs which are active in the above-mentioned diseases.

The present invention further relates to a model for studying the regulation of the genes present in human adipocytes, characterized in that it consists of immortalized preadipocytes according to the invention or mature adipocytes obtained from said immortalized preadipocytes.

The present invention further relates to a process for studying the affinity of a receptor expressed by adipocytes for one or more given ligands, which process comprises:

bringing the immortalized preadipocytes according to the invention into contact with at least one substance capable of converting them to adipocytes, bringing the mature adipocytes obtained into contact with the given ligands, and detecting an affinity reaction between said adipocytes and said given ligands.

The present invention further relates to lipolytic compositions, characterized in that they comprise mature adipocytes obtained from the immortalized preadipocytes according to the invention.

The present invention further relates to pharmaceutical compositions for controlling obesity, characterized in that they comprise mature brown adipocytes obtained from the immortalized preadipocytes according to the invention, optionally in association with at least one pharmaceutically acceptable vehicle.

The present invention further relates to anti-adipocyte antibodies, characterized in that they are obtained by immunizing an appropriate animal with mature adipocytes obtained by the process for converting the immortalized preadipocytes to mature adipocytes according to the invention.

Such antibodies are particularly suitable for use in the immunotherapy of obesity, especially by eliminating the excess adipocytes.

The present invention further relates to nucleic acid sequences from the lines according to the invention, characterized in that they are capable of expressing at least one of the following proteins: β1- and β2-adrenergic receptors, uncoupling protein, Glut1 and Glut4, and lipoprotein lipase (LPL).

The present invention further relates to a kit for detecting the possible affinity of a ligand for a protein expressed by an adipocyte, characterized in that it comprises:

a culture of preadipocytes according to the invention, means of converting said preadipocytes to mature adipocytes, and one or more control ligands.

Apart from the foregoing provisions, the invention also includes other provisions which will become apparent from the following description referring to Examples of how to carry out the process forming the subject of the present invention, and to the attached drawings, in which:

FIG. 1 illustrates the products expressed by the immortalized preadipocytes according to the invention, FIG. 2 shows the differentiation of the preadipocytes in culture, FIG. 3 shows the products expressed by the adipocytes obtained from the preadipocytes according to the invention, and FIG. 4 illustrates the effect of a number of β agonists on lipolysis.

It must be clearly understood, however, that these Examples are given solely in order to illustrate the subject of the invention, without in any way implying a limitation.

EXAMPLE 1

Line of human brown preadipocytes according to the invention

1) Isolation of preadipocytes of human origin:

Brown adipose tissue is taken from an 18-month-old child suffering from a nephroblastoma.

The stromal vascular cells are obtained from this tissue by digestion with collagenase using the method described by HAUNER et al. (J. Clin. Invest., 1989, 84, 1663–1670).

The brown adipose tissue is treated as follows:

2 mg/ml of collagenase A (Boehringer) in a KRBH (Krebs-Ringer Bicarbonate) buffer, also comprising 20 mg of bovine serum albumin (BSA)/ml, are brought into contact with said tissue; digestion is effected for 40 min at 37° C., with stirring (water bath, 100 rpm).

A first filtration on nylon (pore diameter: 190 $\mu$m) is performed and the remaining fragments are then digested again for 30 min with the same collagenase-based solution and also filtered on a nylon membrane with a pore diameter of 190 $\mu$m.

The cellular suspensions obtained are centrifuged at 200 g for 10 min.

The cellular residue is washed with a Krebs-Ringer buffer containing bovine serum albumin (BSA) and then with the culture medium; the residue contains the preadipocytes.

The cells are treated with Gey's solution in order to remove the erythrocytes.

The cells obtained (preadipocytes) are inoculated into Petri dishes of diameter 35 mm containing 2 ml of a culture medium which comprises DMEM/HAM F12 (1:1, vol/vol) containing 100 U/ml of penicillin, 0.1 mg/ml of streptomycin, 7.5% of calf serum and 2.5% of newborn calf serum (Boehringer).

The inoculation density is 20,000 cells/cm$^2$.

The cultures are maintained at 37° C. for 16 hours in an atmosphere containing 10% of $CO_2$ and 90% of air.

After adhesion, the cells are washed in PBS and the culture medium is renewed and consists of 2 ml of an ITT medium (DMEM/Ham's F12 (1:1, v/v) and glutamax I, containing 33 $\mu$M biotin, 17 $\mu$M pantothenate, 15 mM Hepes, 0.2 nM triiodothyronine (T3), 100 U/ml of penicillin and 0.1 mg/ml of streptomycin), 7.5% of calf serum and 2.5% of newborn calf serum.

The medium is changed every 2 days.

2) Immortalization:

The cells obtained in this way are transfected by microinjection with a construction comprising the sequence coding for the SV40 large T antigen under the control of the vimentin promoter (Hu Vim 830-T/t).

The plasmid containing this sequence is described in European patent application no. 90402009.6; it expresses the T antigen and the t antigen of the SV40 virus and is obtained as follows:

The fragment –830–+93 of the vimentin promoter is cloned into plasmid pUC18; the clones are obtained by digestion of the 5' sequence of the vimentin gene at the site of the restriction enzyme PvuII.

Plasmid pUC18 containing the DNA fragment of the vimentin promoter is linearized with the restriction enzyme XbaI; this gives a sticky 3' end, which is adjusted to give a blunt end, after which the resulting DNA fragment of the vimentin promoter is linked to the DNA fragment of the T antigen by ligation of the XbaI 3' end of the promoter with the SfiI end of the SV40 fragment.

The BamHI 5' and 3' ends are linked in the presence of T4 ligase.

The sequences coding for the T antigen are thus under the control of the vimentin regulatory region of 830 base pairs.

The cells transfected in this way are cultivated on the same medium without T3; when they reach confluence, they are treated with trypsin once a week so as to allow a weekly passage.

This gives the cell line of immortalized preadipocytes called PAZ-6.

3) Characteristics of the cell line of immortalized preadipocytes PAZ-6:

The immortalized brown preadipocytes called PAZ-6 can be cultured (weekly passage) for several months without losing their morphological characteristics or their molecular markers identifiable by PCR.

differentiation into mature adipocytes:

At any time, the immortalized brown preadipocytes obtained can be converted to adipocytes by treatment with insulin and dexamethasone; this conversion is characterized by the accumulation of multilobar fats and by the expression of the specific markers of the adipocytes, namely the $\alpha 2_A$- and β3-adrenergic receptors, and the expression of lipoprotein lipase.

The conditions of conversion are as follows:

The cells are inoculated at a density of 10,000 cells/cm$^2$ and cultivated for 3 days in a medium containing 6% of foetal calf serum in order to obtain confluence; an ITT medium (DMEM/HAM F12 medium supplemented with biotin, pantothenate, Hepes, T3, penicillin and streptomycin, as defined above) is then added to said cells, said medium also containing 0.1 $\mu$M dexamethasone, 850 nM insulin, 1 $\mu$M pioglitazone and 0.25 mM IBMX (3-isobutyl-1-methylxanthine) for 4 days. The culture medium is changed every 2 days; differentiation is obtained in about two weeks as follows: after 15 to 21 days under these culture conditions, the cells are washed with PBS and cultured again in a medium which does not contain insulin, dexamethasone or serum but is supplemented with 10 μg/ml of transferrin and 1 nM T3, for 24 hours, before these differentiated cells are used.

The conversion rate is accelerated in the presence of pioglitazone: in fact, the PAZ-6 preadipocytes, in the presence of insulin and dexamethasone, are differentiated into mature adipocytes capable of accumulating fat globules and of effecting lipolysis; however, this differentiation is significantly increased in the presence of pioglitazone.

a. Markers of the immortalized brown preadipocytes and the mature adipocytes obtained from these preadipocytes: β1- and β2-adrenergic receptors, uncoupling protein (UCP), GLUT1 and GLUT4 (cf. FIG. 1); specific markers of the mature adipocytes obtained: $α2_A$- and β3-adrenergic receptors and lipoprotein lipase (FIG. 3); in addition, the presence of numerous mitochondria confirms that these cells are mature brown adipocytes.

Materials and method used:

After differentiation, the mature adipocytes are cultivated for 24 to 48 hours in ITT medium supplemented with 10 μg/ml of transferrin.

The operating conditions are as follows:

The total RNA of the PAZ-6 cells to be analyzed (immortalized preadipocytes or mature adipocytes) is extracted (CATHALA, 1983, DNA, 2, 329–335) and treated for 20 min at 37° C. with 0.3 U of RNase-free DNase I (RQ1 DNase, Promega) per μg of nucleic acid in a medium comprising 40 mM Tris-HCl buffer at pH 7.9, 10 mM NaCl and 6 mM $MgCl_2$, in the presence of 2 U/μl of placental RNase inhibitor (RNasin, Promega). The RNA is then extracted with a phenol/chloroform mixture and precipitated.

The cDNA is synthesized with 100 U of MLV reverse transcriptase (Gibco BRL) with 200 ng of DNase-containing RNA in 10 μl of reverse transcriptase buffer (50 mM Tris-HCl pH 8.3, 75 mM KCl, 3 mM $MgCl_2$ and 10 mM DTT) containing 0.4 mmol/l of each dNTP, 10 μmol/l of random hexanucleotides (Pharmacia, France) and 2 U/μl of placental RNase inhibitor. For the intron-free genes, a check without reverse transcriptase was made in order to verify that the amplification did not result from residual genomic DNA.

The samples are then supplemented with 4 μl of 10×PCR buffer (1×PCR buffer: 50 mM KCl, 10 mM Tris-HCl pH 9.0 at 25° C., 0.1% Triton X-100 and 1.5 mM $MgCl_2$), 0.5 μl of each 25 mM dNTP, 10 μl of 50% DMSO (for the β1-, β2-, β3- and α2-receptors and adipsin), 0.5 μl of sense and antisense oligonucleotides, each being 25 mM, 1 U of Taq DNA polymerase (Promega) and water ad 40 μl.

The cDNAs are denatured for 2 minutes at 94° C. and amplified with 29 thermal cycles (94° C., 15 s; 60° C., 30 s; 72° C., 30 s) followed by 3 minutes of final extension at 72° C. in a thermal cycling system (GeneAmpPCR System 9600, Perkin-Elmer Cetus).

The sequences of the sense and antisense oligonucleotides and the size of the amplification products are as follows:

β1-AR:
oligonucleotide sequences:
5'-TCGTGTGCACCGTGTGGGCC-3' (SEQ ID NO: 1) and 5'-AGGAAACGGCGCTCGCAGCTGTCG-3' (SEQ ID NO: 2);
size of the amplified product: 265 bp;

β2-AR:
oligonucleotide sequences:
5'-GCCTGCTGACCAAGAATAAGGCC-3' (SEQ ID NO: 3) and 5'-CCCATCCTGCTCCACCT-3' (SEQ ID NO: 4);
size of the amplified product: 329 bp;

β3-AR:
oligonucleotide sequences:
5'-ATGGCTCCGTGGCCTCAC-3' (SEQ ID NO: 5) and 5'-CCCAACGGCCAGTGGCCAGTCAGCG-3' (SEQ ID NO: 6);
size of the amplified product: 316 bp (KRIEF, J., Clin. Invest., 1993, 91, 344–349).

UCP:
oligonucleotide sequences:
5'-TAGGTATAAAGGTGTCCTGG-3' (SEQ ID NO: 7) and 5'-CACTTTTGTACTGTCCTGGTGG-3' (SEQ ID NO: 8);
size of the amplified product: 590 bp (CASSARD et al., J. Cell Biochem., 1990, 43, 255–264).

Depending on the type of amplification, two products are obtained:
U=29 PCR cycles
U'=39 PCR cycles β-actin:
oligonucleotide sequences:
5'-GAGACCTTCAACACCCC-3' (SEQ ID NO: 9) and 5'-GTGGTGGTGAAGCTGTAG-3' (SEQ ID NO: 10);
size of the amplified product: 236 bp (FEVE et al., J. Biol. Chem., 1992, 267, 15909–15915);

α2-A:
oligonucleotide sequences:
5'-CGAGCGAGCCAGGTGAAGCC-3' (SEQ ID NO: 11) and 5'-GCCAGCGGAAACCTCACACG-3' (SEQ ID NO: 12);
size of the amplified product: 403 bp (KOBILKA et al., Science, 1987, 238, 650–656);

GLUT1:
oligonucleotide sequences:
5'-TGCTGGCTGTGGGAGGA-3' (SEQ ID NO: 13) and 5'-GAGGATGCCGACGACGAT-3' (SEQ ID NO: 14);
size of the amplified product: 470 bp (MUECKLER et al., Science, 1985, 229, 941–945);

GLUT4:
oligonucleotide sequences:
5'-TCCTGCTGCCCTTCTGTC-3' (SEQ ID NO: 15) and 5'-GGCCTACCCCTGCTGTCT-3' (SEQ ID NO: 16);
size of the amplified product: 309 bp (FUKUMOTO et al., J. Biol. Chem., 1989, 264, 7776–7779);

adipsin:
oligonucleotide sequences:
5'-CGGCTGGGGCATAGTCA-3' (SEQ ID NO: 17) and 5'-GCACGCCCCCGCACACC-3' (SEQ ID NO: 18);
size of the amplified product: 200 bp (WHITE et al., J. Biol. Chem., 1992, 267, 9210–921);

lipase (hormone sensitive) (HSL):
oligonucleotide sequences:
5'-GGGGCTGAGTTTGAGCG-3' (SEQ ID NO: 19) and 5'-GCTCCTCACTGTCCTGTCC-3' (SEQ ID NO: 20);
size of the amplified product: 286 bp (LANGIN et al., Proc. Natl. Acad. Sci. USA, 1993, 90, 4897–4901);

lipase (lipoprotein):
oligonucleotide sequences:
5'-CCTGCTCGTGCTGACTCTG-3' (SEQ ID NO: 21) and 5'-GGGCTCCAAGGCTGTATC-3' (SEQ ID NO: 22);
size of the amplified product: 473 bp (WION KL. et al., Science, 1987, 235, 1638–1641).

The subsequent nucleotide sequences were all determined using the Oligo 4.0 elementary analysis program (National Biosciences, Plymouth, Minn. 5547, USA).

In RT PCR, the same messenger RNAs are identified in the clone and in the line.

Results:

FIG. 1 illustrates the products expressed by the immortalized preadipocytes according to the invention (PAZ-6 line): these preadipocytes express the β1-adrenergic receptor (265 bp), the β2-adrenergic receptor (329 bp) and the α2$_A$-adrenergic receptor (403 bp), UCP (uncoupling protein) (U and U': 590 bp), HSL (hormone sensitive lipase) (H) (286 bp); adipsin (Ad) (200 bp), GLUT1 (G1) (470 bp), GLUT4 (G4) (309 bp) and β-actin (Ac) (336 bp). Each genetic footprint corresponds to 200 ng of initial total RNA, from which the cDNA was amplified as follows: RT PCR for 29 cycles (except U', PCR for 39 cycles) carried out with (+) or without (−) reverse transcriptase.

M corresponds to the 123 bp ladder marker.

Figure 3:
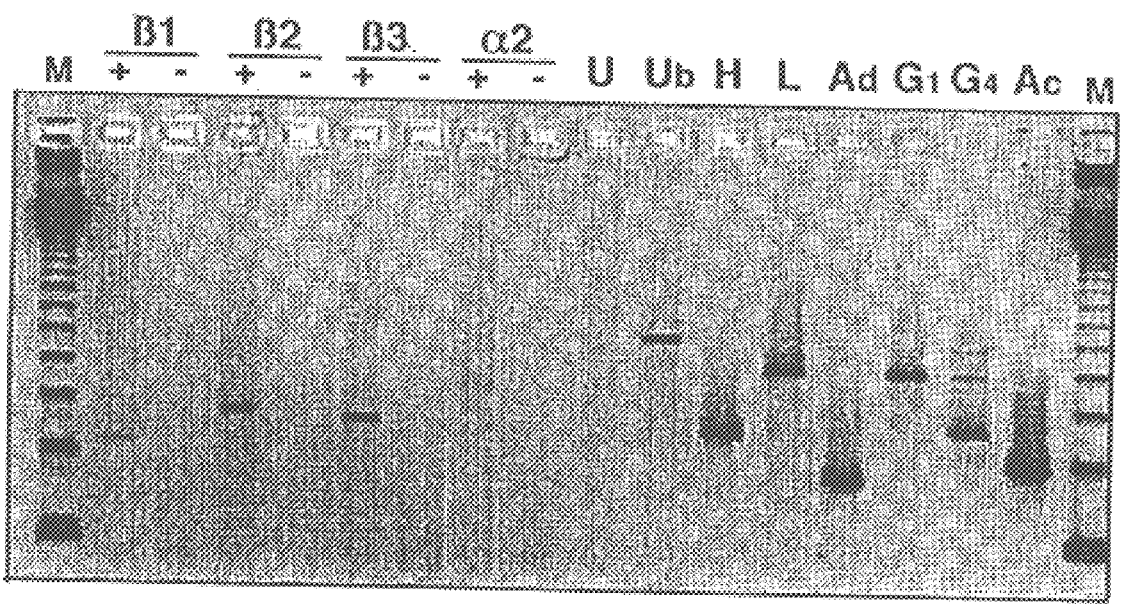
FIG. 3 shows the markers expressed by the adipocytes, especially the β3-adrenergic receptor (β3, 316 bp), the α2$_A$-adrenergic receptor and LPL; moreover, the expression levels of adipsin, HSL, LPL and GLUT4 are greater than those of the preadipocytes.

In addition, these differentiated cells still express UCP (FIG. 3). The UCP mRNA is also present on Northern hybridization.

2 weeks after the conversion to adipocytes, the cells are cultured in a medium devoid of insulin and dexamethasone, which, in the other cell types previously used, resulted in a decrease in the expression of the β3-adrenergic receptor; however, this is not so in the case of the PAZ-6 cells according to the invention.

Figure 1:
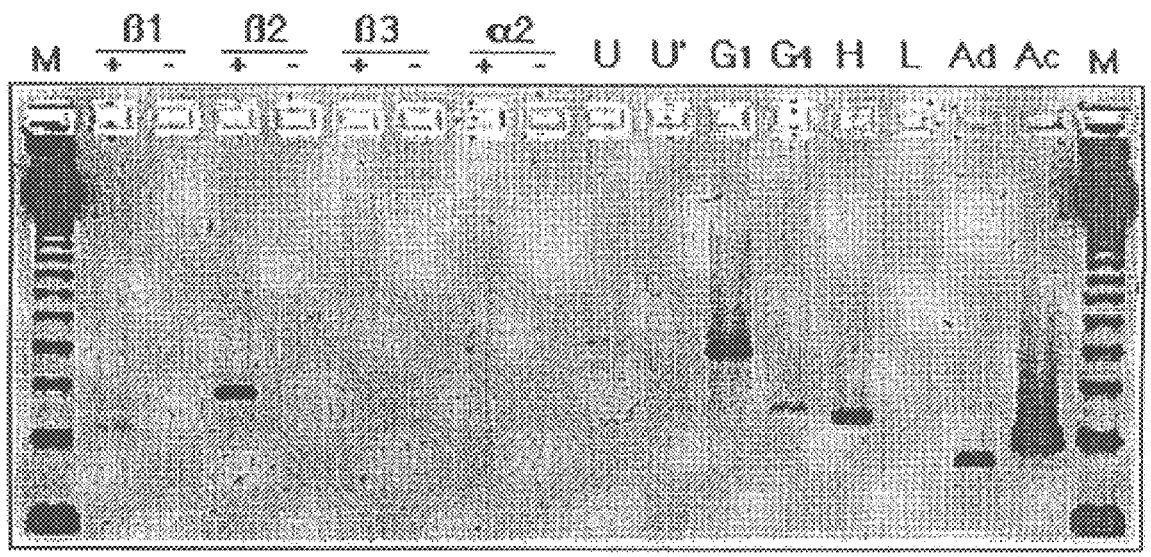
Figure 2:
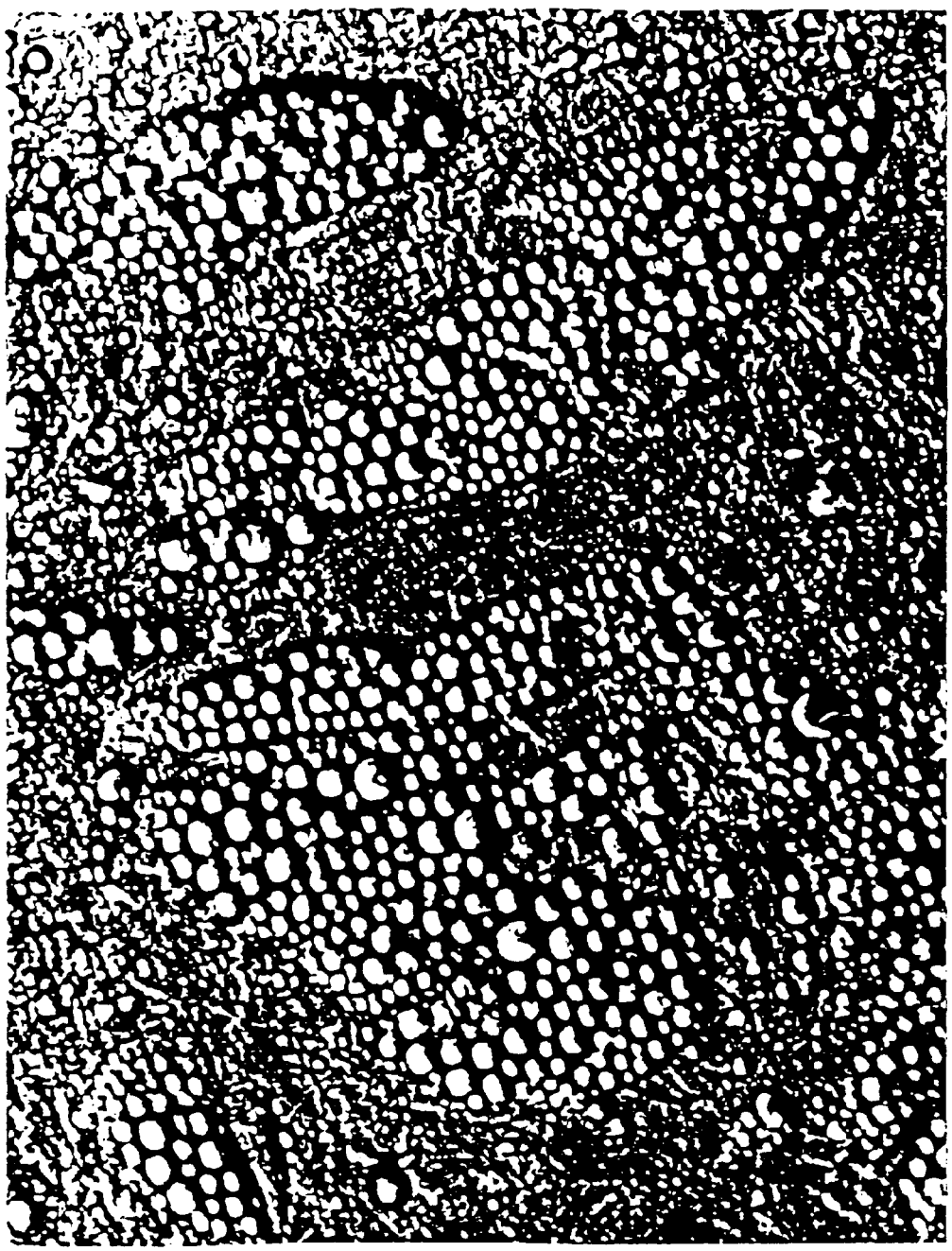
FIG. 2 shows the differentiation of the preadipocytes in culture after confluence in an ITT medium supplemented with T3, insulin and dexamethasone, for 3 weeks.

The RT PCR is carried out under the same conditions as those of FIG. 1 (Ub=U')- 5 μl out of a total of 50 μl were deposited on gel. The image of the gel is a negative image. The same fragments are amplified.

As illustrated above, β3-AR is expressed when the human brown preadipocytes are converted to adipocytes after treatment with insulin, dexamethasone and pioglitazone.

This expression is also observed at the mRNA level with the aid of a moderate PCR amplification (29 cycles) and at the receptor level with the aid of binding assays in the presence of β1 and β2 antagonists (cf. b.).

b. Detection of the β-adrenergic receptors (β-AR)

* determination of the binding sites for the β antagonist ligand iodocyanopindolol (I-CYP) in the PAZ-6 cell line Method:

The cells are washed with PBS, incubated for 5 minutes at 37° C. with a solution of trypsin/2% EDTA and resuspended in DMEM supplemented with 10% (v/v) of horse serum.

After centrifugation at 450×g for 5 minutes at 4° C., the cellular residue is washed twice with PBS and the cells are then resuspended in PBS.

For the binding assays, 100 μl of cellular suspension are incubated (1) in the presence of 500 pM I-CYP and in the presence or absence of 50 μM bupranolol (to define the non-specific bindings), or (2) in the presence of ICI 118551 and/or CGP 20712A (0.1 mM each).

The actual binding assay itself is carried out for 90 min at 25° C. in a final volume of 250 ml of PBS supplemented with 50 mg/ml of bovine serum albumin and 1 mM desipramine.

The reaction is stopped by rapid filtration through a Whatman GF/C glass fibre filter previously immersed for 30 min in a solution of PBS containing 0.3% of polyethyleneimine (to reduce the non-specific bindings).

The protein concentrations are determined by the method of M. Bradford (Anal. Biochem., 1976, 72, 248–256).

Bovine serum albumin is used as the standard and the cellular suspensions are homogenized with a Polytron homogenizer for a maximum of 5 seconds before the reaction.

Results:

In the undifferentiated PAZ-6 line, about 30 fmol of I-CYP binding sites in the isolated membranes are completely blocked with 50 μM bupranolol (the amount of I-CYP sites is therefore about 70 fmol) in the presence of 500 pM I-CYP and 0.05 mM bupranolol (which blocks all the β-specific binding sites: β1-, β2- and β3-AR), as illustrated in Table I below.

In the presence of 100 nM ICI 118551 (specific antagonist of β2-AR sites), the I-CYP binding sites are reduced by 46%.

The presence of β1-AR sites is verified by using CGP 20712A, a specific antagonist of β1-AR sites, at a concentration of 10 nM. Under these conditions, 58% of the I-CYP binding sites are inhibited. The two antagonists used simultaneously result in an 86% reduction (inhibition) of the number of binding sites.

This indicates that the I-CYP binding sites in the undifferentiated PAZ-6 cells are mostly β1- and β2-adrenergic sites in equimolar amounts.

After differentiation of the PAZ-6 line, the presence of about 20 fmol of I-CYP binding sites is determined under the same conditions as those described above. In the presence of the specific antagonist of β2-AR sites, ICI 118551, the number of binding sites is reduced by 34%. In the presence of the specific antagonist of β1-AR sites, CGP 20712A, a 35% reduction is observed. The two antagonists used simultaneously reduce the number of binding sites by 64%.

This result indicates the presence of β1- and β2-adrenergic sites in equimolar amounts and the presence of β3 sites, which constitute at least 36% of the total number of I-CYP binding sites.

TABLE I

| | | Accumulation of cAMP | | | |
|---|---|---|---|---|---|
| | | pmol cAMP/mg protein | | Multiplication factor/basal level | |
| Cell type | Differentiation | basal | ISO | CGP12177A | ISO | CGP12177A |
| PAZ-6 | no | 201 ± 30 | 4344 ± 1060 | 254 ± 167 | 21 ± 2 | 1.3 ± 1 |
| PAZ-6 | yes | 130 ± 26 | 2083 ± 1420 | 323 ± 129 | 15 ± 7 | 2.4 ± 0.5 |

ISO = isoprenaline

* accumulation of cAMP in the PAZ-6 cell line

Insofar as no specific antagonist of β3-AR sites exists, direct proof of the presence of β3-AR cannot be obtained on the basis of determining the I-CYP binding sites. However, a specific partial agonist of β3-AR sites does exist (CGP 12177A), which antagonizes the β1- and β2-AR sites; consequently, an accumulation of cAMP after stimulation with CGP 12177A will provide direct proof of the presence of β3-AR.

Method:

The following method is used to determine the intracellular levels of cAMP:

The cells are washed once in PBS and incubated in the absence or presence of 10 mM isoprenaline or CGP 12177A, for 15 min at 37° C., in a buffer comprising PBS, 0.5 mM IBMX and 0.5 mM ascorbic acid.

The incubation buffer is removed and the cells are lyzed in 1 M NaOH for at least 20 min at 37° C. The lyzate is neutralized with 1 M acetic acid and centrifuged in a microcentrifuge at maximum speed for 5 min.

The supernatant is used to determine the cAMP (cAMP-$^3$H kit, Amersham).

Results:

Stimulation of the undifferentiated PAZ-6 cells with isoproterenol (10 μM) activates all the β-adrenergic receptors and causes a 21-fold increase in the cAMP levels. CGP 12177A (β1 and β2 antagonist and partial β3 agonist) does not cause any significant stimulation of the adenylyl cyclase, confirming the absence of functional β3-adrenergic receptors in these undifferentiated PAZ-6 cells.

Stimulation of the differentiated PAZ-6 cell line with isoproterenol (10 μM) activates all the β-AR sites (15-fold increase in the cAMP level/basal level), whereas CGP 12177A causes a stimulation of only 20% (2.4-fold increase in the cAMP level), suggesting the presence of a significant number of β3-adrenergic receptors coupled with the adenylyl cyclase).

This partial stimulation can be explained by the presence of β1- and β2-AR, which are not stimulated by CGP 12177A, and by the partial agonist properties of this compound. This result is compatible with the above conclusion, which states that the I-CYP binding sites which cannot be blocked by β1- and β2-AR antagonists but can be blocked by bupranolol are β3-AR binding sites.

c. Lipolysis assay (on the PAZ-6 line):

Method:

The lipolysis test consists in measuring the amount of glycerol generated by the mature adipocytes treated with lipolytic ligands.

Monolayers of (differentiated) mature adipocytes in culture plates (6 wells) are washed and preincubated overnight in DMEM/Ham's F12 (1:1, v/v) comprising 1% of fatty acid-free BSA. The cells are then incubated in a Krebs-Ringer phosphate buffer (pH 7.4) comprising 2% of fatty acid-free BSA, 4.5 g/l of glucose, 50 μg/ml of $Na_2S_2O_5$ and the β-adrenergic ligands, in a volume of 500 μl, for 2 hours at 37° C.

The glycerol level is measured on 100 μl of incubation medium by following the reduction of NAD to NADH at 340 nm in the presence of 10 μg/ml of glycerol dehydrogenase (derived from *Enterobacter aerogenes*, Boehringer Mannheim) in the following reaction buffer: $K_2CO_3$/$NaHCO_3$ 125 mM pH 10, NAD 3.5 mM and $(NH_4)_2SO_4$ 330 mM.

Figure 4:
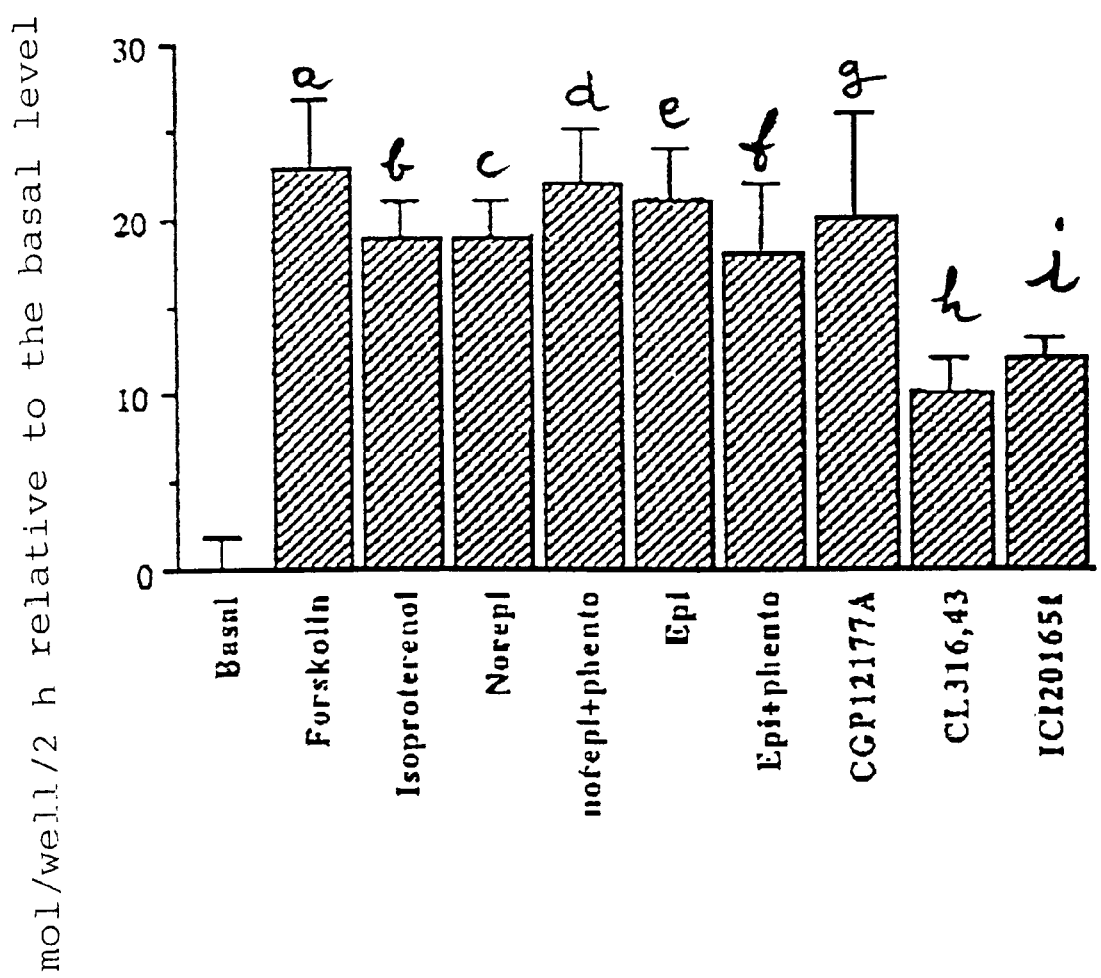

Results:

The results are shown in FIG. 4, which illustrates the results obtained for different β agonists: forskolin $10^{-4}$ M (column a), isoproterenol $10^{-5}$ M (column b), norepinephrine $10^{-5}$ M (column c), mixture of norepinephrine $10^{-5}$ M+phentolamine 20 μg/ml (column d), epinephrine $10^{-5}$ M (column e), mixture of epinephrine $10^{-5}$ M+phentolamine 20 μg/ml (column f), CGP 12177A $10^{-5}$ M (column g), CL 316,43 $10^{-5}$ M (column h), ICI 201651 $10^{-5}$ M (column i), expressed in nmol/well/2 hours relative to the basal level.

The results illustrated in FIG. 4 show lipolysis induced by an agent which directly stimulates the adenylyl cyclase (forskolin) and by β1-AR and β2-AR agonists (isoproterenol, norepinephrine and epinephrine), in the presence or absence of an α2-adrenergic antagonist (phentolamine). Lipolysis is also seen to be induced by specific agonists of β3-AR (β1-AR and β2-AR antagonists like CGP 12777A, CL 316,43 and ICI 20651). These observations suggest that most of the lipolysis induced by isoproterenol in the differentiated PAZ-6 human adipocytes is controlled by the β3-adrenergic receptors.

d. Expression of the Ob gene in the differentiated PAZ-6 cells:

The differentiated PAZ-6 cells express the human equivalent of the product of the murine Ob gene.

When it is injected, leptin (Ob protein) apparently reduces appetite and hence obesity in Ob mice in which the corresponding gene is mutant. In man, no mutation of the Ob gene was observed and the concentration of the Ob protein is significantly increased in obese subjects.

The simultaneous appearance of β3-AR and the product of the Ob gene in the differentiated PAZ-6 mature adipocytes suggests the existence of a link between these two proteins.

In particular, the treatment of rat adipocytes with the β3 agonist CL 316,43 seems to reduce substantially the levels of mRNA coding for the Ob protein.

The fact that the Ob gene is expressed in PAZ-6 adipocytes is totally surprising. In fact, the Ob protein has hitherto been essentially considered as playing a role in the regulation of satiety. Its detection in brown adipocytes suggests that it plays a role in thermogenesis.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. A cell line comprising immortalized human preadipocytes containing a nucleic acid fragment having at least one immortalizing fragment of a viral oncogene and at least one promoter selected from the group consisting of the promoter of said viral oncogene and the promoter of the human vimentin gene, wherein said immortalized human preadipocytes (a) express at least one of the following proteins: β1- and β2-adrenergic receptors, upcoupling protein (UCP), glucose transporters Glut1 and Glut4, and lipoprotein lipase (LPL); and (b) are capable of being converted to mature human adipocytes which produce fat, contain numerous mitochondria, express the $\alpha 2_A$- and β3-adrenergic receptors as well as the expression product of the Ob gene, and have an inverted ratio Glut4/Glut1 relative to said immortalized human preadipocytes.

2. The cell line according to claim 1, wherein said cell line is derived from brown adipose tissue.

3. The cell line according to claim 1, wherein said cell line is derived from white adipose tissue.

4. The cell line according to claim 1, wherein the immortalizing fragment comprises of a sequence coding for the T antigen of the SV40 virus.

5. The cell line according to claim 1, wherein the promoter is selected from the group consisting of the SV40 T oncogene promoter and the human vimentin promoter.

6. The cell line according to claim 5, wherein the human vimentin promoter comprises the nucleic acid fragment of the human vimentin gene promoter between bases –878 and +93 of the regulatory sequence of human vimentin.

7. The cell line according to claim 5, wherein the human vimentin promoter comprises bases –830 to –140 located upstream of the CAP site.

8. The cell line according to claim 5, wherein the human vimentin promoter comprises a nucleic acid fragment selected from the group consisting of the nucleic acid sequence of bases –830 to –539 and the nucleic acid sequence of bases –540 to –140 located upstream of the CAP site.

9. The cell line according to claim 1, wherein said cell line is PAZ-6 having the Collection Nationale de Culture de Microorganismes (CNCM) accession number I-1531.

10. A process for the preparation of immortalized human preadipocytes comprising converting preadipocytes from a human adipose tissue by introducing therein a nucleic acid sequence comprising at least one immortalizing fragment of a viral oncogene and at least one promoter selected from the group consisting of the promoter of said viral oncogene and the promoter of the human vimentin gene.

11. A process for converting the cell line of claim 1 to mature adipocytes, comprising culturing said cell line in a medium comprising insulin.

12. A process according to claim 11, wherein said medium further comprises at least one of the following compounds: glucocorticoid, triiodothyronine (T3), β-adrenergic receptor agonists, NPY, and melatonin.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear -continued

```
    (ii) MOLECULE TYPE: other nucleic acid
         (A) DESCRIPTION:  /desc = "PRIMER"

(xi) SEQUENCE DESCRIPTION: SEQ ID NO: 1:

TCGTGTGCAC CGTGTGGGCC                                              20

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
         (A) DESCRIPTION:  /desc = "PRIMER"

(xi) SEQUENCE DESCRIPTION: SEQ ID NO: 2:

AGGAAACGGC GCTCGCAGCT GTCG                                         24

(2) INFORMATION FOR SEQ ID NO: 3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
         (A) DESCRIPTION:  /desc = "PRIMER"

(xi) SEQUENCE DESCRIPTION: SEQ ID NO: 3:

GCCTGCTGAC CAAGAATAAG GCC                                          23

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
         (A) DESCRIPTION:  /desc = "PRIMER"

(xi) SEQUENCE DESCRIPTION: SEQ ID NO: 4:

CCCATCCTGC TCCACCT                                                 17

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION:  /desc = "PRIMER"

(xi) SEQUENCE DESCRIPTION: SEQ ID NO: 5:

ATGGCTCCGT GGCCTCAC                                                18

(2) INFORMATION FOR SEQ ID NO: 6:

(i) SEQUENCE CHARACTERISTICS:
        (A) LENGTH: 25 base pairs
        (B) TYPE: nucleic acid
```

(C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO: 6:

CCCAACGGCC AGTGGCCAGT CAGCG                                                  25

(2) INFORMATION FOR SEQ ID NO: 7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO: 7:

TAGGTATAAA GGTGTCCTGG                                                        20

(2) INFORMATION FOR SEQ ID NO: 8:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO: 8:

CACTTTTGTA CTGTCCTGGT GG                                                     22

(2) INFORMATION FOR SEQ ID NO: 9:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO: 9:

GAGACCTTCA ACACCCC                                                           17

(2) INFORMATION FOR SEQ ID NO: 10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO: 10:

GTGGTGGTGA AGCTGTAG                                                          18

-continued

```
(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 11:

CGAGCGAGCC AGGTGAAGCC                                               20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 12:

GCCAGCGGAA ACCTCACACG                                               20

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 13:

TGCTGGCTGT GGGAGGA                                                  17

(2) INFORMATION FOR SEQ ID NO: 14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO: 14:

GAGGATGCCG ACGACGAT                                                 18

(2) INFORMATION FOR SEQ ID NO: 15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"
```

(xi) SEQUENCE DESCRIPTION: SEQ ID NO: 15:

TCCTGCTGCC CTTCTGTC                                              18

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "PRIMER"

(xi) SEQUENCE DESCRIPTION: SEQ ID NO: 16:

GGCCTACCCC TGCTGTCT                                              18

(2) INFORMATION FOR SEQ ID NO: 17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "PRIMER"

(xi) SEQUENCE DESCRIPTION: SEQ ID NO: 17:

CGGCTGGGGC ATAGTCA                                               17

(2) INFORMATION FOR SEQ ID NO: 18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "PRIMER"

(xi) SEQUENCE DESCRIPTION: SEQ ID NO: 18:

GCACGCCCCC GCACACC                                               17

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "PRIMER"

(xi) SEQUENCE DESCRIPTION: SEQ ID NO: 19:

GGGGCTGAGT TTGAGCG                                               17

(2) INFORMATION FOR SEQ ID NO: 20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear

```
    (ii) MOLECULE TYPE: other nucleic acid
         (A) DESCRIPTION:  /desc = "PRIMER"

(xi) SEQUENCE DESCRIPTION: SEQ ID NO: 20:

GCTCCTCACT GTCCTGTCC                                                    19

(2) INFORMATION FOR SEQ ID NO: 21:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: other nucleic acid
         (A) DESCRIPTION:  /desc = "PRIMER"

(xi) SEQUENCE DESCRIPTION: SEQ ID NO: 21:

CCTGCTCGTG CTGACTCTG                                                    19

(2) INFORMATION FOR SEQ ID NO: 22:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION:  /desc = "PRIMER"

(xi) SEQUENCE DESCRIPTION: SEQ ID NO: 22:

GGGCTCCAAG GCTGTATC                                                     18
```